United States Patent [19]  
Fabinski et al.

[11] Patent Number: 4,496,840
[45] Date of Patent: * Jan. 29, 1985

[54] NONDISPERSIVE INFRARED GAS ANALYZER

[75] Inventors: Walter Fabinski, Hattersheim; Udo Deptolla, Ober-Olm, both of Fed. Rep. of Germany

[73] Assignee: Hartmann & Braun AG, Frankfurt, Fed. Rep. of Germany

[*] Notice: The portion of the term of this patent subsequent to Jul. 28, 1998 has been disclaimed.

[21] Appl. No.: 289,184

[22] Filed: Aug. 3, 1981

[30] Foreign Application Priority Data

Aug. 8, 1980 [DE] Fed. Rep. of Germany ....... 3030002

[51] Int. Cl.$^3$ ............................................. G01J 1/00
[52] U.S. Cl. .................................. 250/343; 250/345; 250/352
[58] Field of Search ................ 250/343, 344, 345, 352

[56] References Cited
U.S. PATENT DOCUMENTS 3,925,667 12/1975 Staab ............................... 250/344 X
4,281,248 7/1981 Fabinski et al. ................ 250/343 X
4,373,137 2/1983 Fabinski et al. ..................... 250/343

FOREIGN PATENT DOCUMENTS 53478 4/1977 Japan .................................. 250/343

Primary Examiner—Janice A. Howell
Attorney, Agent, or Firm—Ralf H. Siegemund

[57] ABSTRACT

A nondispersive, two-beam, infrared gas analyzer with two differently long measuring gas cells and differential detectors is improved by gilt detection cell interiors and absorbing rods in the detector cell which is in line with the shorter measuring gas cell. Adjustable absorption permits suppression of cross sensitivity errors.

9 Claims, 3 Drawing Figures

NONDISPERSIVE INFRARED GAS ANALYZER

BACKGROUND OF THE INVENTION

The present invention relates to a nondispersive infrared gas analyzer. Such gas analyzers are used, for instance, for detecting pollutants such as carbon monoxide in the air of interior rooms or in the exhaust gases of automobiles, etc.

Gas analyzers of the type to which the invention pertains are, for example, constructed to include an infrared measuring beam path and a reference beam path; and a chopper, or the like, modulates these radiation beams. Each of the beam paths includes a cell containing or being passed through by a measuring gas; but the two cells are of different lengths. The radiation beams are separately detected by receiver cells containing the particular component whose concentration in the measuring gas is to be detected. The two receiver cells are interconnected by a differential pressure sensor which includes a capacitor with a deflective membrane electrode.

A gas analyzer of the type described above is, for example, disclosed in our U.S. Pat. 4,281,248, issued July 28, 1981 (see also German printed patent application No. 28 27 345). This patent deals with a particular approach to reduce the so-called cross sensitivity of such an analyzer which arises when a particular component in the measuring gas has an absorption band overlapping an absorption band of the component to be detected. In accordance with that patent, a movable interference filter is partially inserted in the measuring beam path, affecting but a portion thereof. The present invention is related to an alternative approach which is believed to be more effective.

It should be mentioned that in our U.S. Pat. No. 4,281,248 we have suggested to include radiation-absorbing elements in the receiver cell of that radiation path which contains the shorter one of the two cells being flown through by the measuring gas. The same receiver or detection cell is internally provided with black walls; the other one has gilted walls. This particular arrangement reduces any interference. The present invention is an improvement of this earlier attempt to eliminate cross sensitivity.

DESCRIPTION OF THE INVENTION

It is an object of the present invention to provide a new and improved nondispersive infrared gas analyzer.

It is a particular object of the present invention to provide a new infrared gas analyzer which includes infrared radiation-measuring and reference beam paths being periodically interrupted and which, further, includes a differential pressure-sensing device having receiver or detection cells and a membrane capacitor, and which further includes cells of different lengths, being passed through by the gas to be analyzed and being disposed in the beam paths in that the shorter cell is disposed in the reference path, the longer one in the measuring path.

In accordance with the preferred embodiment of the present invention, it is suggested to improve an analyzer as per the particular object by constructing the receiver cells to have essentially similar configurations, at least as far as the the interior walls and volumes are concerned; and the receiver cell in the reference path is to contain several thin, black wires or rods having a low heat capacity. Fine-tuning for error suppression may require compensating means such as a diaphragm or filter structure at least in front of the reference path receiver cell, primarily for indirectly affecting the amount of radiation absorbed by the rods or wires. Adjustment of these compensating means will be a part of the calibration and setup procedure for the equipment. The two measuring cells are preferably gilded on the inside and the rods are preferably made of graphite.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

Proceeding now to the detailed description of the drawings, FIG. 1 illustrates a source 1 of infrared radiation and a beam divider 2 establishes two radiation beams, a measuring beam, and a reference beam. The two beam paths are respectively identified by path axes, axis 3 for the reference beam and axis 4 for the measuring beam. Both radiation beams are periodically interrupted by a diaphragm disk 5 which is driven by a motor 5a at a constant speed.

Figure 1:
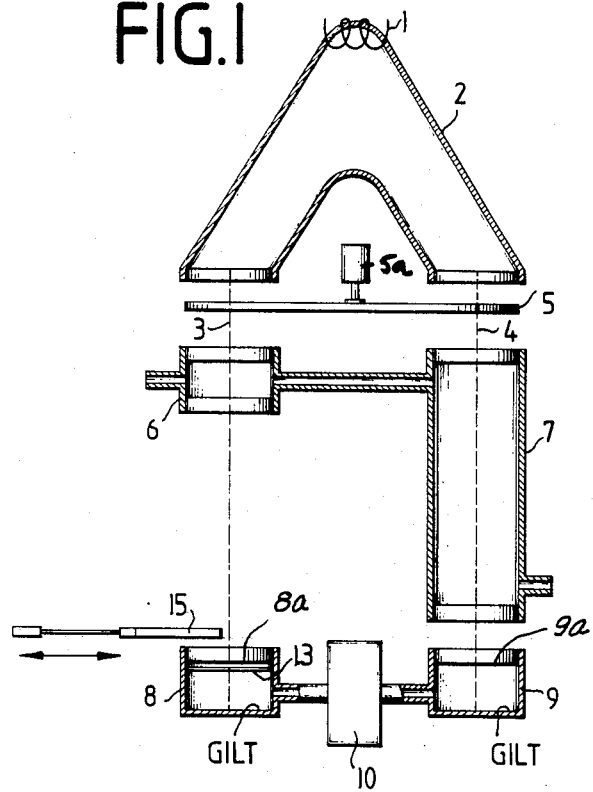
FIG. 1 illustrates, somewhat schematically and partially in sections, a first example of the preferred embodiment of the invention for practicing the best mode thereof in conjunction with measuring the CO content of ambient air.

The measuring gas, which in this case is indoor air, is first fed into a relatively short cuvette or cell 6 in the reference path; and a communicating duct leads to an inlet near one end of a relatively long cell 7 in the measuring path. The air is discharged from the other end of that cell 7. These cells 6 and 7 are provided with conventional entrance and exit windows.

Radiation, permitted to leave the cells 6 and 7, is respectively intercepted by measuring receiving or detection cells 8 and 9, having entrance windows 8a and 9a. These cells are filled with CO, and they are both connected to opposite sides of a measuring chamber 10 which includes a flexible membrane being one electrode of a measuring and pick-up capacitor. The membrane flexes in one direction or the other, depending upon the sign of the pressure differential as between the two cells 8 and 9. The capacitor converts the deflection of this one of its electrodes into an electrical signal which is representative of the pressure differential. This electrical signal can be used conventionally to extract therefrom information representing the CO content in the measuring gas.

Turning now to further particulars, the two cells 8 and 9 are gold-plated or gilded along their respective interior walls, excepting, of course, the respective entrance windows 8a and 9a. Moreover, these cells are otherwise similar in respect to their volume and interior configuration, gilded wall surfaces of both cells are a particular and preferred way of rendering these cells similar in all respects, including particularly a low absorption rate.

Figure 2:
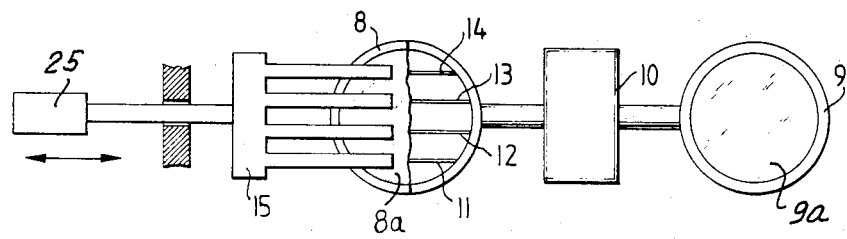
FIG. 2 is a top elevation of the analyzer shown in FIG. 1, but including further details.

The cell 8 contains, in addition, four small, black-surfaced rods or wires 11, 12, 13, and 14, disposed therein side by side as can be seen best in FIG. 2. These rods or wires are thin, elongated elements having a low heat capacity but a high rate of absorption of all infrared radiation that they intercept. The rods or wires are preferably made of graphite. The spacing of these rods is quite regular as depicted.

A comb-shaped diaphragm 15 is disposed outside cell 8, but the prongs are situated in optical alignment with the rods; that is to say, these prongs of the comb can be so aligned, but the comb as a whole can be retracted so that only portions of the rods are shaded in this manner by the prongs.

The figures show four rods and four diaphragm prongs; this number is, of course, arbitrary to some extent, but was not chosen merely for reasons of descriptive convenience, rather for a realistically usable number. Reference numeral 25 refers to a drive for the diaphragm to position the prongs as is deemed necessary and desirable.

In the case of CO measurement, water vapor in the air (host gas) must be deemed an interfering component because water has absorption bands overlapping those of CO. The $CO_2$ content is negligable. Assuming the short cell 6 is 40 mm long and the long cell 7 is 210 mm long, and further assuming four rods of a 0.2 mm diameter each, one obtains a rather low measuring error of not more than 4.5% CO in the range of from 0 ppm to 100 ppm CO and at a rather high water vapor content, corresponding to saturation at 24° C. Moreover, the diaphragm was fully retracted for this range of measurement. An advance of the diaphragm and its prongs permits further reduction of the measuring error, down to practically 0.

A somewhat simpler form (and not quite as effective) of adjustment is obtained by placing a partically absorbing nonfrequency selective) filter in front of chamber 8. Still alternatively the rods 11 to 14 may be retractably mounted in tubular holders which do not extend into the interior of cell 8, but the rods may be partially retracted into these tubes. Retracting these elements 11 to 14 is another way of adjustment of the degree of absorption obtained in order to achieve the compensation needed for full error suppression.

The retraction may be carried out through external application of a magnetic field so that the sealing integrity of the cell 8 is not impaired. This method of adjustment is as good as the one described, but more expensive. The comb-shaped diaphragm is deemed the preferred way of effecting the requisite adjustment toward error reduction.

Figure 3:
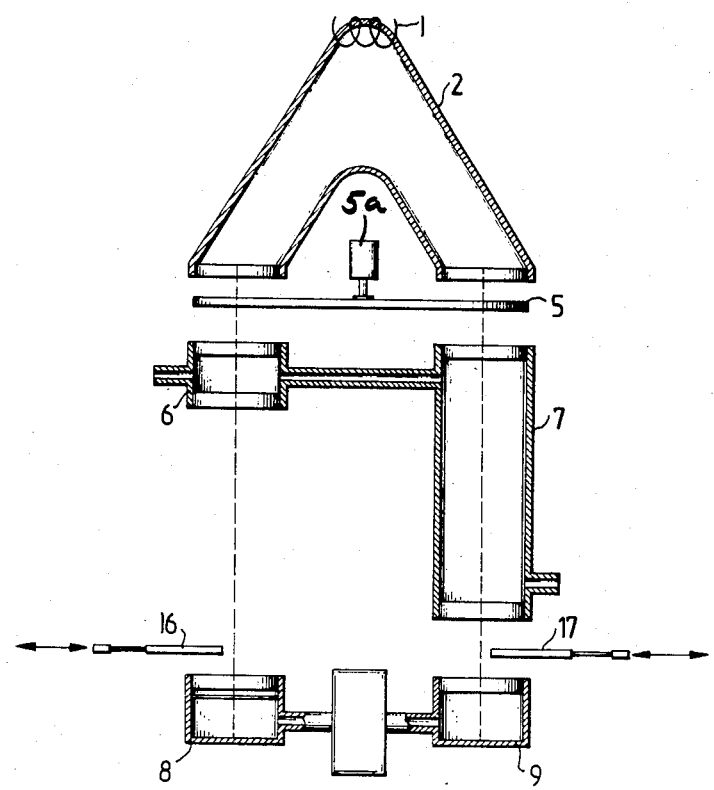
FIG. 3 illustrates a second example of the preferred embodiment of the invention for practicing the best mode thereof in conjunction with measuring the CO content of diluted automobile exhaust gases.

Turning now to the example shown in FIG. 3, many components are similar to those shown in FIGS. 1 and 2; that is to say, the overall construction follows the same principles. This includes particularly the two-beam source means 1 and 2, the chopper wheel 5, and the measuring gas cells 6 and 7, although their dimensions may differ because the objective of the device, presently described, is to measure the concentration of CO in diluted automobile exhaust fumes. The basic difference of these examples resides in the details of the adjusting structure for error suppression.

The device includes an adjustable interference filter 16 which is a long-wave pass filter, being transmissive for long-wave infrared from approximately 4,470 nm and longer. This filter is disposed in front of cell 8 in order to intercept in parts the reference beam. An interference edge filter 17 is disposed in front of the other measuring cell (9). Filter 17 is a short-wave infrared pass filter, passing infrared radiation from approximately 5,000 nm and shorter.

Interfering gas components in this particular instance are again $H_2O$, but also $CO_2$. Still, upon properly adjusting the interference filters, the CO concentration could be detected in a range of up to 100 ppm with an error rate not exceeding +1 ppm; even when the $CO_2$ content would amount up to 30,000 ppm and at a moisture content corresponding to saturation at 24° C.

The measurement is generally particularly difficult for relatively low CO concentrations. In the case of higher concentrations, the filters are not needed; but the configuration of cell 8 suffices to suppress cross sensitivity errors from interfering gas components.

The invention is not limited to the embodiments described above; but all changes and modifications thereof, not constituting departures from the spirit and scope of the invention, are intended to be included.

We claim:

1. Nondispersive infrared gas analyzer which includes a particular component in a host gas, the host gas including at least one component having one or more infrared absorption bands which overlap an infrared absorption band of the particular component, the analyzer including:
   (a) a measuring beam path and a reference beam path without a reference gas and means for providing infrared radiation beams of the same frequency band to the two paths,
   (b) a modulating means for the beams,
   (c) a first, relatively short, cell being passed through by the gas to be analyzed and being disposed in one of said paths,
   (d) a second, relatively long, cell being also passed through by the gas to be analyzed and being disposed in another one of said paths,
   the improvement comprising in combination: a pair of substantially similarly configured receiver cells disposed respectively in said paths and being filled with the gas of said particular component, there being differential pressure-sensing means coupled to the receiver cells and producing a signal representative of the concentration of the particular component in the host gas; and
   a plurality of thin rod or wire elements having a black surface and low heat capacity, and being disposed inside one of the receiver cells being disposed in the path that includes the relatively short cell.

2. Nondispersive infrared gas analyzer which includes a particular component in a host gas, the host gas including at least one component having one or more infrared absorption bands which overlap an infrared absorption band of the particular component, the analyzer including:
   (a) a measuring beam path and a reference beam path without a reference gas and means for providing infrared radiation beams of the same frequency band to the two paths,
   (b) a modulating means for the beams,
   (c) a first, relatively short, cell, being passed through by the gas to be analyzed and being disposed in one of said paths, (d) a second, relatively long, cell being also passed through the gas to be analyzed and being disposed in another one of said paths, (e) a pair of receiver cells disposed respectively in said paths and being filled with the gas of said particular component, (f) differential pressure-sensing means coupled to the receiver cells and producing a signal representative of the concentration of the particular component in the host gas, the improvement comprising:

the receiver cells having substantially identical interior configurations;

a plurality of elongated thin rod-like elements having high radiation-absorptive properties and a low heat capacity, and being disposed inside the cell of the pair of cells which is disposed in said reference path; and compensating means for adjusting the amount of radiation absorbed by the elements.

3. Analyzer as in claim 1 or 2, said rod or rod-like elements being made of graphite.

4. Analyzer as in claim 3, said receiver cells having gilded interior wall surfaces.

5. Analyzer as in claim 2, the compensating means including a comb-shaped diaphragm for adjustably shading the rod or rod-like elements.

6. Analyzer as in claim 2, the compensating means including at least one interference filter in front of the cell containing the rod-like elements.

7. Analyzer as in claim 6, the compensating means further including a second interference filter in front of the respective other cell.

8. Analyzer as in claim 7, said filters having different, nonoverlapping infrared passage ranges.

9. Analyzer as in claim 7, said one filter being a low pass filter of up to approximately 4475 nm at highest frequency, the second filter being a high pass filter for passage of radiation of from approximately 5000 nm and higher infrared frequencies.

* * * * *